United States Patent [19]

Blaser et al.

[11] Patent Number: 4,719,801
[45] Date of Patent: Jan. 19, 1988

[54] ULTRASONIC METHOD AND APPARATUS FOR DETECTING LEAKS

[75] Inventors: Dwight A. Blaser, Fraser; Kestutis P. Nemanis, Redford Township, Wayne County; James J. Zik, Rochester; Edward C. Hess, Farmington Hills, all of Mich.

[73] Assignee: General Motors Corporation, Detroit, Mich.

[21] Appl. No.: 908,621

[22] Filed: Sep. 18, 1986

[51] Int. Cl.⁴ ............................................. G01N 29/00
[52] U.S. Cl. ............................................. 73/592; 73/40
[58] Field of Search ................ 73/592, 40, , 600, 619; 340/550; 901/44, 46

[56] References Cited

U.S. PATENT DOCUMENTS

| 2,378,237 | 6/1945 | Morris. | |
| 3,782,180 | 1/1974 | Harris | 73/592 |
| 4,275,597 | 6/1981 | Quedens et al. | 73/618 |
| 4,290,309 | 9/1981 | Charlebois et al. | 73/621 |

FOREIGN PATENT DOCUMENTS 289047  8/1971  U.S.S.R. ................... 73/40

Primary Examiner—Jerry W. Myracle
Attorney, Agent, or Firm—Warren D. Hill

[57] ABSTRACT

Seals in an automotive body are inspected for leaks by sensing ultrasonic energy passing through a seal. Either of an ultrasonic emitter or detector is scanned along a seal outside the body by a robot and the other is inside the body. The emitter operates at frequencies of 65 to 80 kHz and repetitively sweeps through a range of 6 kHz. The body may be either open or closed.

6 Claims, 6 Drawing Figures

ULTRASONIC METHOD AND APPARATUS FOR DETECTING LEAKS

FIELD OF THE INVENTION

This invention relates to detecting leaks by ultrasonic techniques and particularly to the detection of leaks in automotive vehicle bodies.

BACKGROUND OF THE INVENTION

In the manufacture of automotive vehicles it is necessary to inspect each vehicle for leaks so that any deficiencies can be corrected. Very small opening in door or window seals as well as in sealant-filled joints between panels can admit air or water or simply may be the source of wind noise. The prior practice has been to spray water on a vehicle body and visually locate leakage. This requires that the body be completed with all seals in place but seats and other soft trim which may be damaged by leaking water should not yet be installed. This severely restricts the assembly procedures as well as the inspection process. In addition, many leaks are not detectable with the water test.

It is desirable, therefore, to detect leaks on either closed or open vehicle bodies in any stage of assembly. To meet this objective it has been attempted to use ultrasonic leak detection. Prior to this invention, the ultrasonic procedures were limited to inspection of closed bodies and were ineffective for small leaks, especially those which define a tortuous path, and thus were not acceptable inspection techniques.

SUMMARY OF THE INVENTION

It is therefore an object of the invention to provide a method and apparatus for reliably detecting leaks in vehicle bodies which may be either open or closed.

The invention is carried out by a method of detecting leaks in a vehicle body having seals separating the inside and outside of the body, comprising the steps of; irradiating the seals on either side of the body with ultrasonic energy having a frequency above about 65 kHz, repetitively sweeping the ultrasonic energy through a frequency range, sensing the energy passed through the body whereby the sensed energy is low in the absence of a leak and measurably higher in the presence of a leak, and determining the location of a leak as well as the presence of a leak by limiting one of the irradiating action and the sensing action to a local region, moving the local region along the seal, and correlating the time of sensing high energy to a leak location.

The invention is further carried out by an apparatus for inspecting an automotive vehicle for leaks comprising; a first transducer comprising an ultrasonic emitter, means for driving the emitter to sweep the emitted energy through a frequency range having a center frequency above about 65 kHz, a second transducer comprising an ultrasonic receiver responsive to the emitted energy, robot means for scanning one of the transducers along a predetermined path outside the vehicle to define a moving inspection zone, the other transducer inside the vehicle so that the ultrasonic energy is received by the receiver at a low level if no leak is present in the inspection zone and if the inspection zone is moved to a leak location an increase in received energy is indicative of a leak, and a computer coupled to the robot and to the receiver programmed to respond to the detection of a leak and identify the location of the leak.

BRIEF DESCRIPTION OF THE DRAWINGS

The above and other advantages of the invention will become more apparent from the following description taken in conjunction with the accompanying drawings wherein like reference numerals refer to like elements and wherein.

DESCRIPTION OF THE PREFERRED EMBODIMENT

In the assembly of an automotive vehicle, sheet metal panels are spot welded together to form seams which are strong but not always watertight. To preclude leaks a bead of sealant, usually comprising a polymer, is applied over the seam. To assure proper sealing it is desirable to test the integrity of the seal at an early stage of vehicle assembly so that the seams are still accessible and necessary repairs can be made inexpensively. The test itself is often much easier and sometimes is possible only before additional components are installed. Another major reason for early inspection is to identify, as soon as possible, any assembly procedures that cause leaks. Fixed glass, such as the windshield, is installed in a vehicle opening by a polymer molding and adhesive. Door openings are provided with weatherstripping which can leak if not properly installed, and movable glass windows slidably fit into resilient channels to provide a seal. Each of these seals is subject to leaks and must be inspected to assure freedom from wind noise and water or dust leakage.

Leaks are detected ultrasonically by exposing one side of a seal to ultrasound and measuring the sound level on the other side. If the seal is sound, only a low level or background noise is detected, but a high level is detected if there is a leak. By concentrating on a localized inspection zone and scanning the zone along a seal, the detected signal peaks where a leak is encountered and thus the position as well as the mere existence of a leak can be determined. To be practical in an automotive assembly application, the method must be practiced with automatic equipment such as robots and other mechanisms for positioning the sources and receivers and scanning along the seals. It is also desirable to simultaneously scan several regions to quickly complete the inspection.

The ultrasonic source or emitter may be either inside or outside the vehicle with the microphone or receiver on the other side. It is preferred to place the receivers outside the vehicle, especially in the case of a closed vehicle, for ease in collecting the signals and identifying which of several receivers is adjacent the leak. Robots move the receivers along programmed paths adjacent the seals and the emitters are placed inside the vehicle either manually or automatically.

Figure 1:
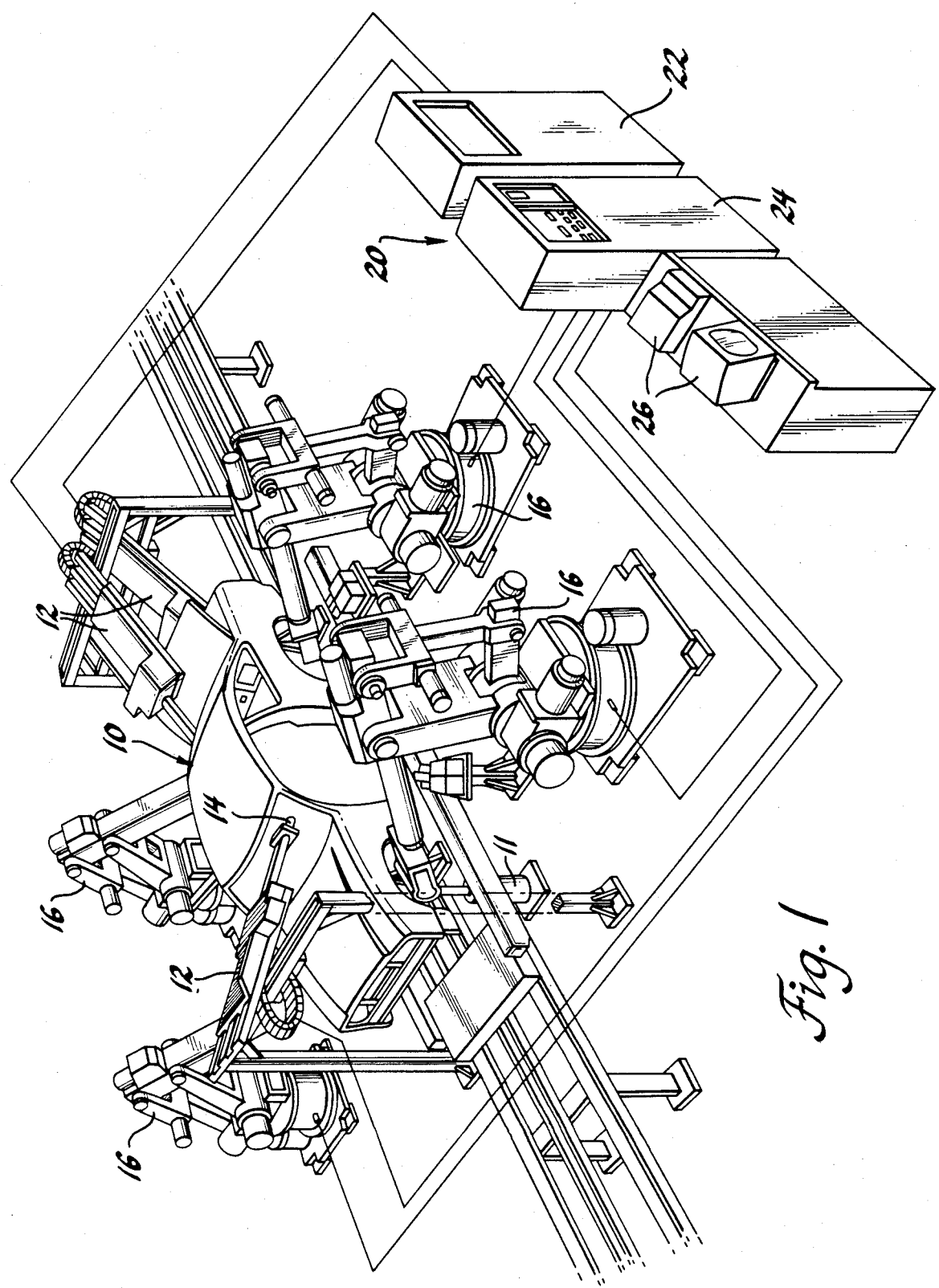
FIGS. 1 and 2 are perspective views of leak detection stations equipped to practice the invention.

FIG. 1 shows a partially assembled body 10 without glass or doors positioned in an inspection station equipped for underbody inspection. The body is elevated by lifts 11 to facilitate access to the underbody. Motor driven slides 12 carrying ultrasonic emitters 14 intrude into the body through the windshield and backlight openings and into the trunk compartment to strategically place the emitters for irradiation of the seals to be inspected. Two robots 16 on each side of the body maneuver receivers (not shown) along underbody seams, seeking signals indicative of leaks. Electronic equipment 20 near the inspection station is coupled to the robots, slides, and transducers to control the operation and analyze the resulting receiver signals. The equipment 20 includes a programmable controller 22 and a computer 24 with peripheral equipment 26. In another station after the windshield and backlight are installed, equivalent equipment is used to insert emitters into the body through the door openings and robots scan the receivers around the glass seals.

Figure 2:
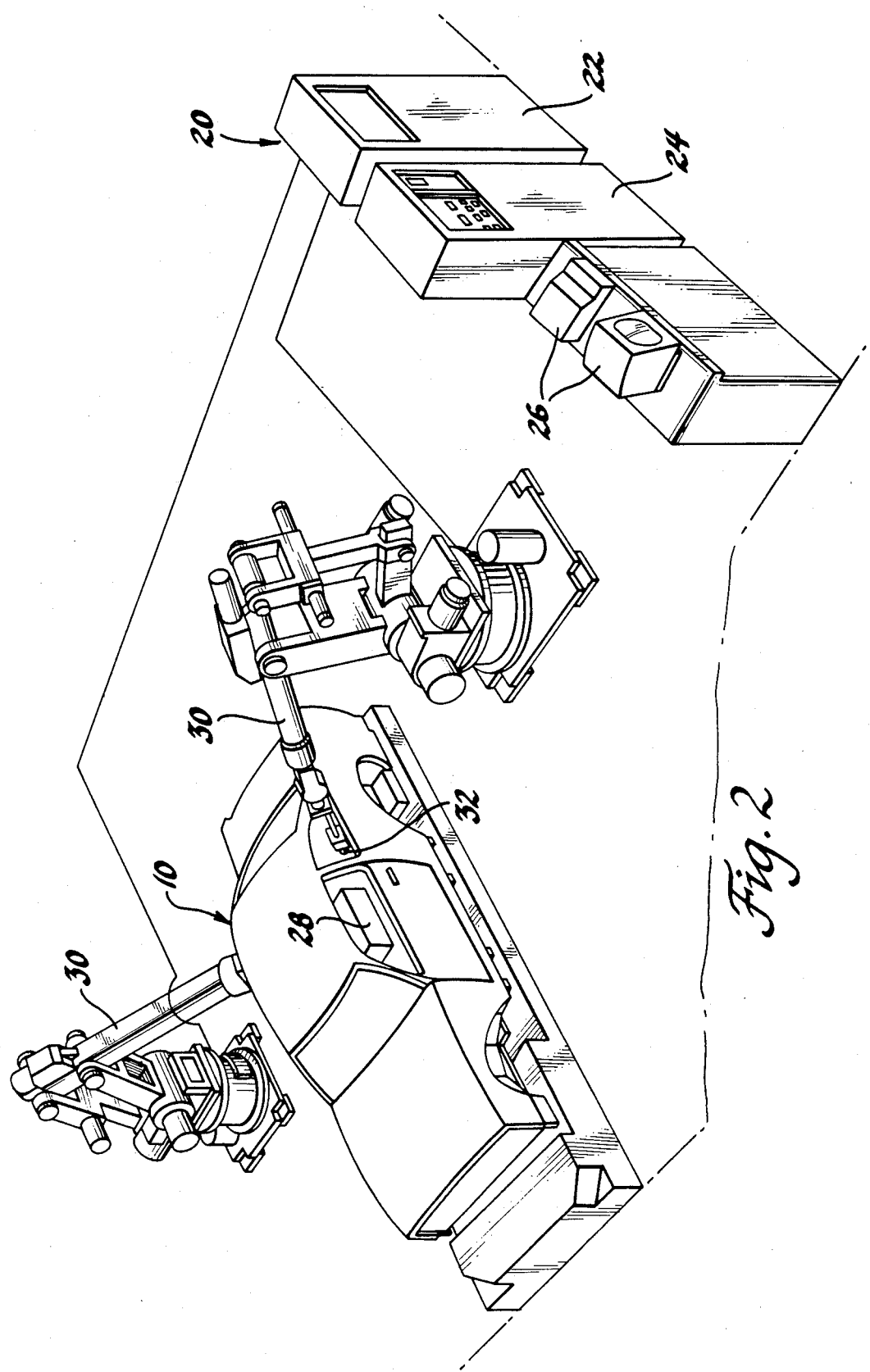

FIG. 2 shows still another inspection station for bodies that are completely closed with all glass in place. A battery operated emitter assembly 28 is manually placed inside the vehicle body and robots 30 with receivers 32 scan along the outside of the door and side window seals to complete the inspection not performed in previous stages of assembly. The emitter assembly 28 may contain several emitters or speakers positioned for optimum results.

Figure 3:
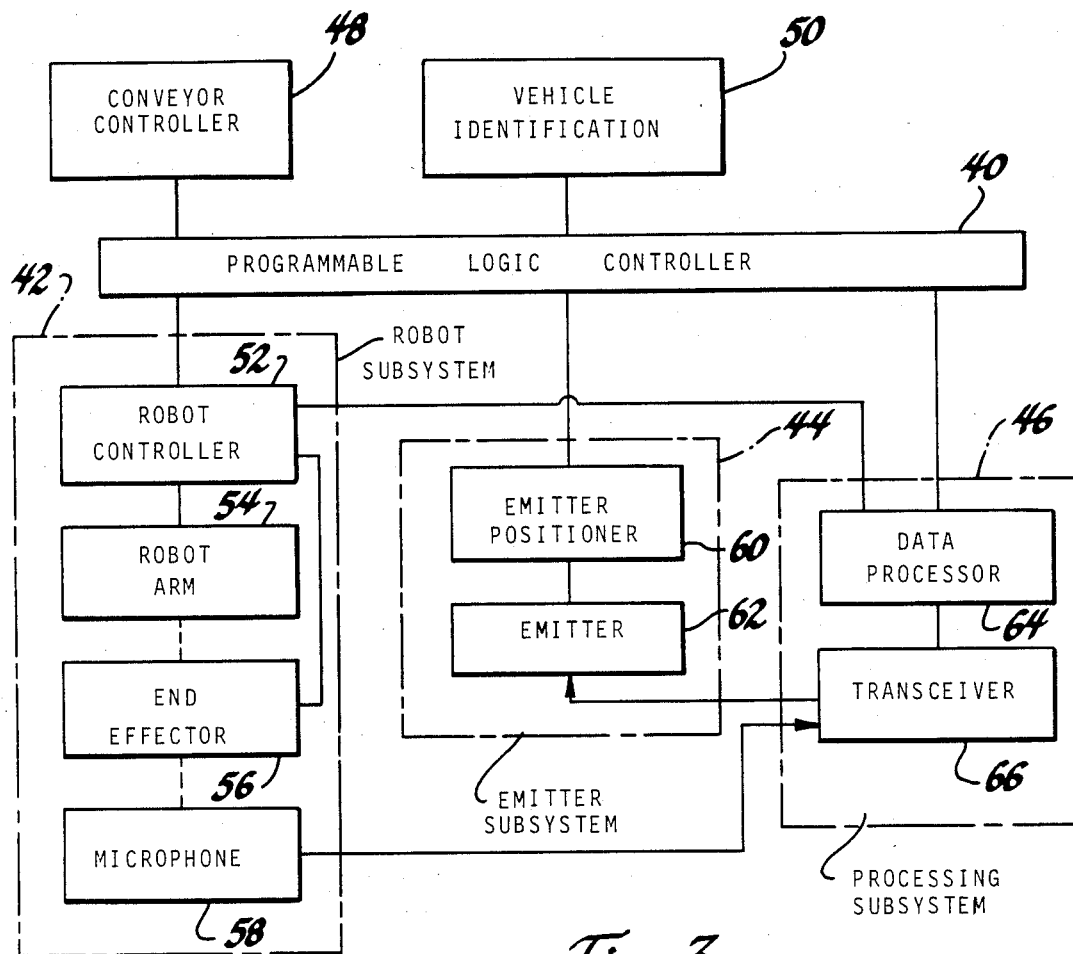
FIG. 3 is a block diagram of the leak detection system according to the invention.

The interconnection of the equipment is depicted in the subsystem block diagram of FIG. 3. A programmable logic controller 40, such as the Allen-Bradley PLC model number 2/30, coordinates the subsystems including the robot subsystem 42, the emitter subsystem 44 and the processing subsystem 46. A plurality of robot subsystems is preferred even though one is shown. The controller 40 has further connections to such devices as a conveyor controller 48 for positioning the body in the station, and an automatic vehicle identification device 50 for instructing the robot which of several preprogrammed paths to follow for the current body. The robot subsystem may employ an Asea IRB/60 robot, for example, and comprises a robot controller 52 and a robot arm 54 with an end effector 56 and microphone 58. The robot controller is electrically connected to the programmable controller 40 and to the end effector 56. The emitter subsystem 44 includes the motor controlled slide or emitter positioner 60 and the speaker or emitter 62. The processing subsystem 46 includes a computer such as a Motorola VME data processor 64 and an ultrasonic transceiver 66 which is connected to both the microphone 58 and the emitter 62. The data processor 64 is coupled to the controller 40 and to the robot controller 52. The computer is responsive to the robot controller output and to the microphone signal and is programmed to detect a leak when the microphone signal increases to a level above the background noise and to determine the leak location on the basis of which robot corresponds to the detected leak, the time of the leak detection, and the robot position at the time of the leak detection. When a battery operated emitter assembly 28 is used the emitter control can be included in the assembly.

A variant of the leak detection system which is not illustrated in the drawings comprises placing the emitters outside the body under robot control and placing the receivers inside the body. Each emitter is driven in a frequency range different from the others and the receivers are each tuned to a particular range. This allows separation of signals to avoid cross-talk and enables the computer identification of a seal leak location.

A major problem in prior attempts at ultrasonic leak detection was the development of standing waves in the body cavity so that the seal areas were nonuniformly irradiated by sonic energy and some regions received nearly no irradiation. This problem is overcome, according to this invention, by rapidly and repeatedly sweeping the emitted frequency over a bandwidth sufficient to break up or prevent the standing wave pattern. A band width of 6 kHz was found to be adequate, while narrower bandwidths resulted in reduced effectiveness.

Figure 4:
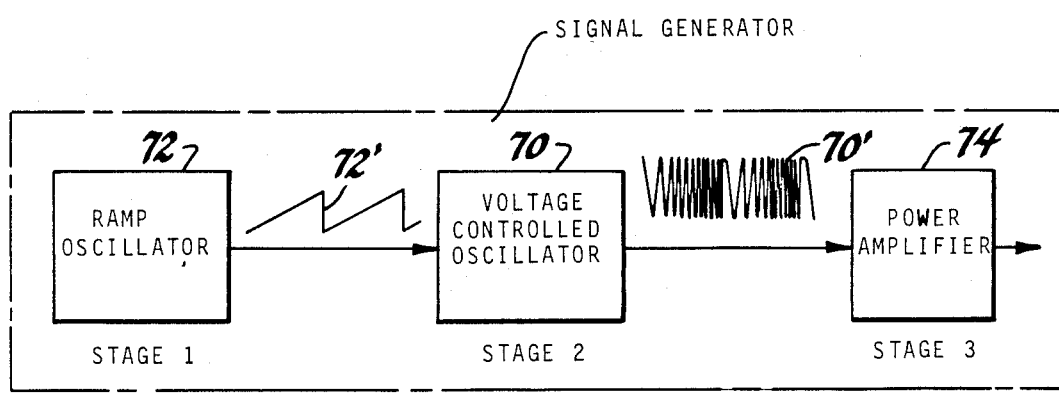
FIG. 4 is a block diagram of signal generating circuitry including the waveforms produced for carrying out the invention.

The swept frequency, also known as a chirp signal, is produced by the circuit of FIG. 4 which comprises a voltage controlled oscillator (VCO) 70 connected to the output of a ramp oscillator 72. The VCO drives a power amplifier 74 which is coupled to the emitter. FIG. 4 also illustrates the ramp oscillator signal 72' and the VCO output signal 70' which is the same as the emitter output. The ramp voltages are selected such that the VCO frequency varies over a 6 kHz band at a desired center frequency. A ramp frequency of about 200 Hz yields a useful chirp rate. A triangular waveform can be used instead of the ramp signal.

Figure 5:
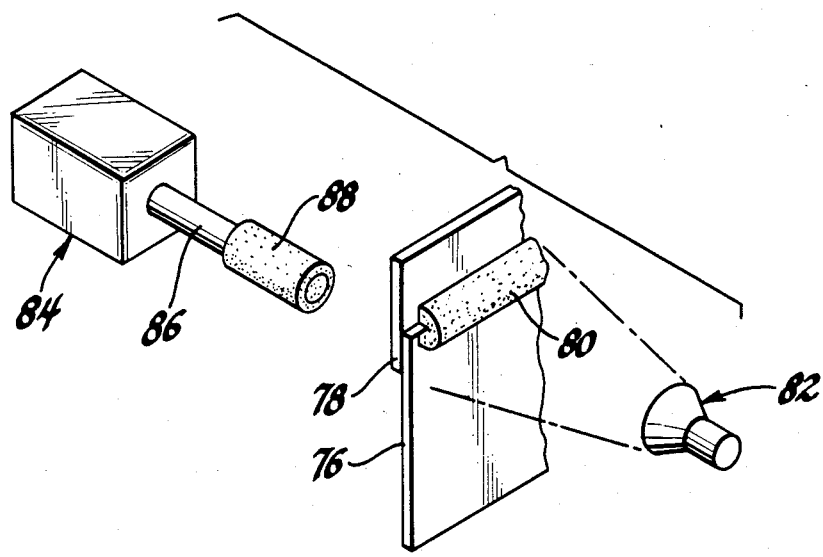
FIG. 5 is a view of an emitter and receiver in operating position in accordance with the invention.

The emitter may be a Polaroid electrostatic transducer or a Massa ultrasonic air transducer model no. E-153 Type 75. The receiver is preferably a Bruel and Kjaer model number 4135 air condenser microphone. FIG. 5 shows a welded panel 76 having a joint 78 covered by a sealant 80, an emitter 82 on one side of the panel and a receiver 84 on the other side adjacent the joint 78. The receiver 84 has a cylindrical receptor 86 with a ½ inch diameter and a short length of ½ inch I.D. rubber hose extension 88 on the receptor. During the scanning operation the end of the extension is maintained ½ inch from the panel 76. In case of accidental contact the rubber hose prevents damage to the receiver and the body. The receiver normally is responsive to a wide angle of sound direction but the extension limits the incoming sound to a small angle. Thus the receiver becomes highly directional and is insensitive to background noise, even to sound from the emitter 82 which travels around the edge of the panel instead of through the joint. If, however, the receiver is within 2 inches of the edge of a panel, noise from the emitter traveling around the edge can be significant. Two methods are available to avoid a problem with this noise: providing a shield to block the noise and using electronic time discrimination to reject the noise which takes a long path from the emitter to the receiver. If the emitter is more than two inches from an edge or opening, the noise amplitude reaching the receiver is too small to introduce a problem.

Another major problem with prior attempts was that the ultrasonic testing failed to detect many of the smaller leaks and especially those which had a tortuous shape, as in a glass support molding. It was discovered that the limitation was imposed by the standard practice of operation at 40 kHz. It was further discovered that operation in the range of 65 to 80 kHz resulted in the detection of 50% more leaks than at 40 kHz with the additional leaks detected being the smaller ones and the tortuous path leaks. The signal to noise ratio at the preferred range is better than at 40 kHz since the noise transmitted through the panel is much less at the 70 kHz region. Above 80 kHz, however, the signal to noise ratio decreases. At the preferred center frequency of 70 khz the 6 kHz bandwidth results in operation between 67 and 73 kHz. At the chirp rate of 200 cycles per second, a scanning rate of 12 to 18 inches per second yields optimum results. This assumes using the highly directional receiver described above which can resolve the position of a leak to within a fraction of an inch. The limiting factor in obtaining leak position information is the accuracy of the robot which provides information on the receiver position at the time of leak detection.

Figure 6:
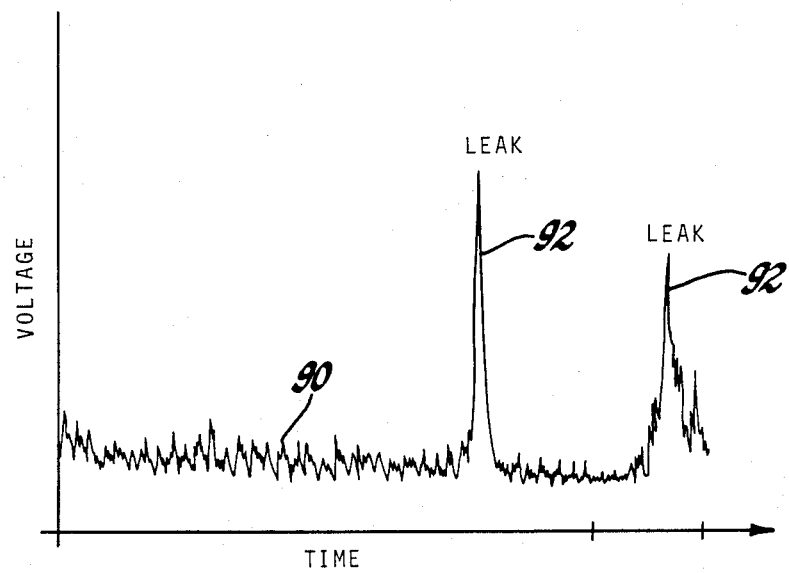
FIG. 6 is a graph of ultrasonic energy detected by a receiver according to the invention.

As shown in FIG. 6, which is a graph of received ultrasonic energy converted to DC voltage, background noise appears as low amplitude waveforms 90 and the leak signals are sharp, well defined high amplitude waveforms 92. Thus the time of a leak detection can be determined accurately. The position of the receiver along the seam is determined by information from the robot controller 52. Standard robot controllers yield such position information to a resolution of about 1½ inches. As the robot scans the receiver along the seam under control of the path program provided through the vehicle identification module 50 and the programmable logic controller 40, the data processor 64 identifies a leak signal received from the emitter 62 and correlates the time of that signal with position data from the controller 52 of the robot subsystem which detected the leak. In that manner the portion of a seal which requires repair is identified. The information is also stored and analyzed for quality control purposes to reveal patterns of leak occurrences which indicate a need for adjustments in the assembly equipment or procedures.

It will thus be seen that the invention provides ultrasonic leak detection method and apparatus which are especially useful for inspection of seals on vehicle bodies and which are effective to find leaks and their positions rapidly and automatically.

The embodiments of the invention in which an exclusive property or privilege is claimed are defined as follows:

1. An apparatus for inspecting an automotive vehicle body for leaks comprising;
   a first transducer comprising an ultrasonic emitter,
   means for driving the emitter to sweep the emitted energy through a frequency range having a center frequency above about 65 kHz,
   a second transducer comprising an ultrasonic receiver responsive to the emitted energy,
   robot means for scanning one of the transducers along a predetermined path outside the body to define a moving inspection zone,
   the other transducer inside the body so that the ultrasonic energy is received by the receiver at a low level if no leak is present in the inspection zone and if the inspection zone is moved to a leak location an increase in received energy is detected, and
   a computer coupled to the robot and to the receiver programmed to respond to the detection of a leak and identify the location of the leak.

2. An apparatus for inspecting an automotive vehicle body for leaks comprising;
   a first transducer comprising an ultrasonic emitter,
   means for driving the emitter to repeatedly sweep the emitted energy through a frequency range of about 6 kHz and having a center frequency between about 65 and 80 kHz,
   a second transducer comprising an ultrasonic receiver responsive to the emitted energy,
   robot means for scanning one of the transducers along a predetermined path outside the body at a scan rate of less than 18 inches per second to define a moving inspection zone,
   the other transducer inside the body so that the ultrasonic energy is received by the receiver at a low level if no leak is present in the inspection zone but if the inspection zone is moved to a leak location an increase in received energy is detected, and
   a computer coupled to the robot and to the receiver programmed to respond to the detection of a leak and identify the location of the leak.

3. An apparatus as defined in claim 2 wherein the body is closed and the robot scans the receiver along the body exterior and the emitter is inside the body.

4. An apparatus for inspecting an automotive vehicle body for leaks comprising;
   a set of ultrasonic emitters outside the body,
   means for driving the emitters to sweep the emitted energy through a frequency range having a center frequency above about 65 kHz, each emitter being operated in a different frequency band,
   a plurality of robots each for scanning one of the emitters along a predetermined path outside the body to define moving inspection zones,
   a plurality of ultrasonic receivers each responsive to one of the emitter frequency bands and located inside the body so that the ultrasonic energy is received by a receiver at a low level if no leak is encompassed by any inspection zone but if an inspection zone is moved to a leak location an increase in received energy occurs, and
   a computer coupled to the robots and to the receivers programmed to respond to the detection of a leak, to identify the receiver of the increased energy, and to identify the location of the leak.

5. The method of detecting leaks in a vehicle body having seals for closing air paths between the inside and outside of the body, comprising the steps of;
   irradiating the seals on either side of the body with ultrasonic energy having a frequency above about 65 kHz,
   repetitively sweeping the ultrasonic energy through a frequency range,
   sensing the energy passed through the body whereby the sensed energy is low in the absence of a leak and measurably higher in the presence of a leak,
   determining the location of a leak as well as the presence of a leak by limiting one of the irradiating action and the sensing action to a local region, moving the local region along the seal, and correlating the time of sensing high energy to a leak location.

6. The method of detecting leaks in a vehicle body having seals in potential leakage paths between the inside and outside of the body, comprising the steps of;
   irradiating seals inside the body with ultrasonic energy having a frequency above about 65 kHz,
   repetitively sweeping the ultrasonic energy through a frequency range on the order of 6 kHz bandwidth,
   sensing the energy passed through the body in a localized inspection zone whereby the sensed energy is low in the absence of a leak and measurably higher in the presence of a leak, and
   determining the location of a leak as well as the presence of a leak by moving the inspection zone along the seal, and correlating the detection of high energy to a leak location.

* * * * *